United States Patent [19]

Mukku

[11] Patent Number: 5,198,340
[45] Date of Patent: Mar. 30, 1993

[54] ASSAY FOR FREE IGF-I, IGF-II, AND GH LEVELS IN BODY FLUIDS

[75] Inventor: Venkat R. Mukku, Fremont, Calif.

[73] Assignee: Genentech, Inc., South San Francisco, Calif.

[21] Appl. No.: 642,509

[22] Filed: Jan. 17, 1991

[51] Int. Cl.⁵ ............... G01N 33/544; G01N 33/566; G01N 33/567

[52] U.S. Cl. ........................ 435/7.8; 424/9; 435/7.9; 435/7.94; 435/29; 435/975; 436/86; 436/501; 436/504; 436/518; 436/531; 436/817

[58] Field of Search .............. 436/518, 815, 501, 531, 436/809, 504, 808, 822, 817, 86; 435/7.9, 7.94, 7.5, 975, 7.95, 29, 7.8; 424/9

[56] References Cited

U.S. PATENT DOCUMENTS

| | | | |
|---|---|---|---|
| 4,005,187 | 1/1977 | Kilthau et al. | 424/1.5 |
| 4,015,939 | 4/1977 | Lewin et al. | 23/230 |
| 4,219,335 | 8/1980 | Ebersole | 23/230 |
| 4,251,360 | 2/1981 | Goldie et al. | 424/1.5 |
| 4,279,885 | 7/1981 | Reese et al. | 424/1 |
| 4,292,296 | 9/1981 | Parsons et al. | 424/1 |
| 4,299,916 | 11/1981 | Litman et al. | 435/6 |
| 4,333,918 | 6/1982 | Carney et al. | 424/1 |
| 4,469,787 | 9/1984 | Woods et al. | 435/7 |
| 4,477,578 | 10/1984 | Miles et al. | 436/518 |
| 4,504,585 | 3/1985 | Reynolds | 424/1 |
| 4,594,327 | 6/1986 | Zuk | 436/514 |
| 4,680,275 | 7/1987 | Wagner et al. | 436/518 |
| 4,704,355 | 11/1987 | Bernstein | 435/6 |
| 4,737,456 | 4/1988 | Weng et al. | 435/7 |
| 4,786,606 | 11/1988 | Giegel | 436/500 |
| 4,791,068 | 12/1988 | Loskotoff et al. | 436/518 |
| 4,818,687 | 4/1989 | Groopman et al. | 436/518 |
| 4,943,522 | 7/1990 | Eisinger et al. | 435/7 |
| 4,956,302 | 9/1990 | Gordon et al. | 436/161 |
| 5,057,417 | 10/1991 | Hammonds et al. | 435/69.1 |

FOREIGN PATENT DOCUMENTS

| | | |
|---|---|---|
| 0155104 | 9/1985 | European Pat. Off. . |
| 0165669 | 12/1985 | European Pat. Off. . |
| 0166623 | 1/1986 | European Pat. Off. . |
| 0221282 | 3/1987 | European Pat. Off. . |
| 0218309 | 4/1987 | European Pat. Off. . |
| 0302673 | 2/1989 | European Pat. Off. . |
| 0375438 | 6/1990 | European Pat. Off. . |
| 85004423 | 2/1985 | Japan . |
| 62-098260 | 5/1987 | Japan . |
| 1098969 | 4/1989 | Japan . |
| WO8809818 | 12/1988 | PCT Int'l Appl. . |
| WO9008957 | 8/1990 | PCT Int'l Appl. . |
| 2203836 | 10/1988 | United Kingdom . |
| 2207245 | 1/1989 | United Kingdom . |
| 8908667 | 9/1989 | World Int. Prop. O. . |

OTHER PUBLICATIONS

Voller et al. "Enzyme Immunoassays in Diagnostic Medicine" Bull. World. Health Organ., vol. 53, pp. 55–65, 1976.

Kricka et al. *Ligand binder assay* pp. 61–110, Marcel Dekker, Inc. New York, N.Y. 1985

Primary Examiner—David Saunders
Attorney, Agent, or Firm—Janet E. Hasak

[57] ABSTRACT

A method and kit are provided for determining levels in a biological sample of free IGF-I, IGF-II, or GH ligand that is normally associated in the sample with a binding protein. This method involves contacting the body fluid with an immobilized unlabeled capture reagent and incubating at 4°–10° C. for no greater than about 4 hours to bind the free ligand contained in the body fluid; separating the fluid from the immobilized capture reagent; and measuring the level of free ligand now bound to the capture reagent. This method is particularly useful to determine levels of free IGF-I in serum or plasma.

19 Claims, 3 Drawing Sheets

ASSAY FOR FREE IGF-I, IGF-II, AND GH LEVELS IN BODY FLUIDS

BACKGROUND OF THE INVENTION

1. Field of the Invention

This invention relates to an assay for detecting the levels of free, circulating insulin-like growth factor-I or -II (IGF-I or -II) or growth hormone (GH) in a body fluid such as plasma or serum not bound to its respective binding protein(s).

2. Description of Related Disclosures

For diagnosing clinical disorders and making decisions regarding appropriate therapy, assay methods have been developed to detect levels of a particular protein indicative of the disorder in a body fluid sample. Since some proteins circulate in the body bound to carrier or binding proteins, assay methods are needed to detect the amount of circulating free protein to obtain an accurate diagnosis. For example, it is desirable to determine blood levels of free IGF-I and GH to diagnose for hypoglycemia, gigantism, acromegaly, hypopituitarism, pituitary dwarfism, GH deficiency, thymomegalia, and CNS diseases such as Alzheimer's disease.

Many assay techniques have been used to detect the somatomedin (IGF) activities of plasma. As is true of most hormones, the original techniques used were bioassays. Salmon and Daughaday, *J. Lab and Clin. Med.*, 49: 825-836 (1957). While such techniques measure a biologic action, they are cumbersome to perform, show a great deal of intra-assay variability, have a relatively high detection limit, are subject to the effects of inhibitory substances, and lack specificity.

The availability of pure peptide for iodination permitted the development of radioreceptor assays (RRA) using tissues as the receptor source. Marshall et al., *J. Clin Endocrinol. Metab.*, 39: 283 (1974); Megyesi et al., *Biochem. Biophys. Res. Commun.*, 57: 307 (1974). A typical RRA protocol involves incubating 100-250 μg of human placental membrane protein with tracer and standards or samples for 16 hours at 2° C., then separating the bound and free ligand by centrifugation. The specificity of this assay is determined by the tracer peptide, but with either IGF-I or IGF-II tracer, there is some cross-reactivity with the other peptide. In contrast, when rat placental membrane is used with IGF-II tracer, a high specificity for IGF-II has been reported. Daughaday et al., *J. Clin. Endocrinol. Metab.*, 53: 289-294 (1981). A IGF-II RRA has been established using ovine placental membranes with a specificity comparable to that of human placental IGF-II RRA and a sensitivity somewhat better than that reported for the rat placental membrane assay. The rat liver plasma membrane RRA preferentially measures IGF-II-related peptides. Although the RRA provides an advance over bioassays in ease of performance and reproducibility, specificity and interference by binding proteins remain problematic.

In the circulation, in other body fluids, and in media conditioned by cultured cells, the somatomedins are bound to specific high-affinity carrier proteins that have been implicated as modulators of IGF actions. The history of IGF binding proteins (BPs) dates back to 1984 when the existence of specific somatomedin carrier proteins in serum was first shown. Hintz, *Clin. Endocrinol. Metab.*, 13: 31-42 (1984). Three distinct IGF BPs have now been cloned and sequenced, and in addition, several other, not yet thoroughly characterized, BP species have been identified in various tissues. On the basis of the sequences it became evident that many of the previously recognized BPs, known by different names, were in fact the same, falling into three classes of cloned BPs. To clarify the present status of these BPs, the Workshop on IGF Binding Proteins, held in Vancouver, Canada, June 1989, proposed the names IGFBP-1, IGFBP-2, and IGFBP-3 for the binding proteins with defined sequences. Ballard et al., *Acta Endocrinol. (Copenh)*. 121: 751-752 (1989). The consensus at the Workshop was that other, incompletely characterized IGFBPs be referred to by size and origin until sequenced.

Amniotic fluid was the first source from which IGFBP-1 was detected. Chochinov et al., *J. Clin. Endocrinol. Metab.*, 44: 902-908 (1977). The protein has been purified also from tissue extract of fetal and maternal placenta and named placental protein. Kiostinen et al., *Endocrinology*, 118: 1375-1378 (1986). The mature protein contains 234 amino acids, predicting a molecular mass of 25.3 kD. Lee et al., *Mol. Endocrinol.*, 2: 404-411 (1988); WO 89/09792 published 19 Oct. 1989. IGFBP-1 migrates on SDS-PAGE at 28-35 kD depending on the stage of reduction. IGFBP-1 is a minor binding protein in serum and contains the unsaturated serum IGF-binding sites. Serum levels are inversely dependent on insulin and have a marked diurnal variation, the levels being highest early in the morning. These levels increase in pregnancy up to several hundred μg/l, and amniotic fluid levels are up to 1000-fold higher than those in serum.

Carrier proteins of the IGFBP-2 class have been isolated from human fetal liver and rat and bovine cell lines. Binkert et al., *EMBO J.*, 8: 2497-2502 (1989). In humans, the mature form contains 289 amino acids and has an apparent molecular mass of 31-40 kD, depending on the stage of reduction on SDS-PAGE. In humans high IGFBP-2 levels have been found in the cerebrospinal fluid. The abundance of this protein in fetal tissue suggests that it has a role in regulating development. IGFBP-2 preferentially binds IGF-II. The majority of serum IGFs are bound to a binding protein composed of two parts forming a complex of molecular mass 125-150 kD. IGFBP-3 is the IGF binding subunit (β-subunit) in this complex. Baxter and Martin, *Proc. Natl. Acad. Sci. USA*, 86: 6898-6902 (1989). It is an acid-stable glycoprotein appearing on SDSPAGE as a major and minor band, corresponding to 53 and 47 kD, respectively. The other components in the complex are the acid-labile, non-IGF-binding subunit (α-subunit) with a molecular mass of 84-86 kD [Baxter, WO 90/0569], and IGF-I or IGF-II (γ-subunit). Sequencing of the cloned cDNA for IGFBP-3 (previously known as IGFBP-53) predicts a molecular mass of 28.7 kD for the non-glycosylated protein and reveals that IGFBP-3 shares 33% sequence identity with IGFBP-1. Wood et al., *Mol. Endocrinol.*, 2: 1176-1185 (1988); Ep 375,438 published 27 Jun. 1990; WO 89/09268 published 5 Oct. 1989.

The levels of IGFBP in adult serum have been found to reflect the growth hormone (GH) status of individuals who are either GH-deficient or acromegalic. Thus, high levels of IGFBP-3 correlate with high levels of GH. Martin and Baxter, *J. Clin. Endo. and Metabol.*, 61: 799-801 (1985). Under normal conditions about 95-98% of the IGF-I in human plasma is bound to the IGFBPs. Studies on size-fractionated human serum, subjected to IGF-I RIA after extraction of each fraction to remove binding activity, have indicated that 72% of the endogenous peptide is associated with the 150-kD fraction and 25% with the 50-kD fraction. Daughaday et al., *J. Clin. Endocrinol. Metab.*, 55: 916-921 (1982).

After acid treatment of the serum to remove endogenous ligands, the IGFBPs (in purified form) have been used as a source of binding sites in competitive protein binding assays for IGF-I. Schalch et al., *J. Clin. Endocrinol. Metab.*, 46: 664-671 (1978); Zapf et al., *Clin. Chem.*, 23: 677-682 (1977). The acid treatment consists of chromatography of serum in dilute acetic acid on gel permeation columns. Binding activity has been reported to emerge between 60 and 80% or between 29 and 46% of the bed volume on Sephadex G-200 depending on the laboratory. To separate IGF-I from endogenous binding protein in samples for assay, each specimen is passed through a Sephadex G-50 column under acid conditions. Fractions emerging between about 50 and 80% of the bed volume are then pooled and assayed. Incubations are for 60-90 minutes at room temperature, after which bound and free ligand are separated using charcoal.

Using IGFBPs from human serum, this technique predominately measures IGF-II. Tracer IGF-II is reported to show three times higher specific binding than tracer IGF-I, and unlabeled IGF-II is more potent in displacing either tracer from binding sites than IGF-I. Zapf et al., *Eur. J. Biochem.*, 87: 285-296 (1978). See also Rechler et al., *Endocrinology*, 107: 1451-1459 (1980). Activity measured by a method that has relative specificity for IGF-II shows relatively poor dependence on GH status. However, a competitive binding assay has been described utilizing a IGFBP released by rat liver explants in organ culture, which preferentially measures IGF-I, although with 50% IGF-II cross-reactivity. Binoux et al., *J. Clin. Endocrinol. Metab.*, 59: 453-462 (1984). An RIA based on IGFBP-2 is described by Drop et al., *J. Clin. Endocrin and Metabol.*, 59: 899-907 (1984).

Since the RRA and IGFBP assays have limitations resulting from specificity and interference by IGFBPs, they are not the preferred tools for making diagnoses or decisions regarding therapy. Therefore, radioimmunoassays (RIA) have been developed. The first successful RIA method for IGF-I was described by Furlanetto et al., *J. Clin. Invest.*, 60: 648-657 (1977), who was able to raise high-affinity antisera with great specificity for IGF-I. With this antisera, the assay shows half-maximal displacement of tracer by about 0.1 ng of IGF-I, with somatomedin-A less than 5% as reactive, and even lower cross-reactions by human and rat IGF-II. RIAs have been developed subsequently by Bala and Bhaumick, *J. Clin. Endocrin. and Metabol.*, 49: 770-777 (1979) and Zapf et al., *J. Clin. Invest.*, 68: 1321-1330 (1981). Moreover, two antisera have been raised against a synthetic carboxy-terminal octapeptide and the 12 amino acid C-peptide region, the two regions of greatest difference between IGF-I and IGF-II, and between the IGF peptides and proinsulin. The one raised against the carboxy-terminal region, when used with intact IGF-I tracer, had very low cross-reactivity with rat and human IGF-II [Hintz et al., *J. Clin. Endocrinol. Metab.*, 51: 672-673 (1980)], while the C-peptide antibody showed no IGF-II cross-reactivity even at 1000 ng/ml. Hintz et al., *J. Clin. Endocrinol. Metab.*, 50: 405-407 (1980). See also Hintz et al., *J. Clin. Endocrinol. Metab.*, 55: 927-930 (1982). For other assays, see, e.g., Hall et al., *J. Clin. Endocrinol. Metab.*, 48: 271-278 (1979); EP 292,656 published 30 Nov. 1988.

Specific assays for human and rat IGF-II have also been developed. See, e.g., Zapf et al., *Metab. Clin. Exp.*, 27: 1803-1828 (1978); Zapf et al., *Acta Endocrinol.*, 95: 505 (1980); Zapf et al., *J. Clin. Invest.*, supra; Hintz and Liu, *J. Clin. Endocrinol. Metabol.*, 54: 442-446 (1982); Moses et al., *Eur. J. Biochem.*, 103: 401-408 (1980). The assays for IGF-II have shown that normally there is a higher content of IGF-II than IGF-I in plasma. This is confirmed by the specific RRA for IGF-II utilizing rat placental membranes.

Also, monoclonal antibodies suitable for IGF-I RIA have been developed. See, e.g., Baxter et al., *J. Clin. Endocrinol. Metab.*, 54: 474-476 (1982); Laubli et al., *FEBS Lett.*, 149: 109-112 (1982).

The RIAs represent an advance in specificity over the RRAs and bioassays, being more specific to IGF-I than IGF-II, and in general are more sensitive than the other assays. They have been used in a variety of clinical disorders and appear to reflect GH status reliably.

The major problem with measuring IGF-I or -II by RIA is interference by IGFBPs. This interference takes a variety of forms. If the IGFBPs bind I-labeled IGF-I preferentially, a false elevation of the plasma IGF-I concentration will occur. If, however, they interfere with the binding of unlabeled IGF-I to antibody, IGF-I levels will be underestimated. Where a monoclonal antibody was used, unextracted samples were almost devoid of activity, even when containing high levels of antigen. The traditional means to overcome this problem is to separate IGFBPs from free peptide by acid gel filtration chromatography before IGF determination. Zapf et al., *J. Clin. Invest.*, supra.

Several investigators have attempted to circumvent the need for chromatography by nullifying the effect of the IGFBPs using various chemical treatments. These include incubation of samples with acid, followed by lyophilization [Bala and Bhaumick, supra] or neutralization [Binoux et al., *Acta Endocrinologica*, 99: 422-430 (1982)]; or the exposure to heparin in the RIA buffer [Furlanetto, *J. Clin. Endocrin. and Metabol.*, 54: 1084-1086 (1982)]. These acid treatment procedures destroy the acid-labile component of the IGFBP complex, but not the acid-stable component.

To avoid these difficulties, a direct RIA that does not depend on prior chemical treatment of samples has been developed in which the plasma is collected in EDTA and the assay is performed in the presence of protamine using an antibody of sufficiently high affinity. Chatelain et al., *J. Clin. Endocrin. and Metab.*, 56: 376-383 (1983). One disadvantage of this method is that only a fraction of the total IGF-I content of plasma is measured. Further, due to the reduced affinity of the IGFBP for IGF-I induced by EDTA, the value obtained will vary greatly depending on the amount of time that the sample has incubated at temperatures greater than 4° C.

For those RIAs where extraction is used, a nonequilibrium incubation protocol in which samples and standard are incubated with antibody for several days before addition of tracer, may be required to ensure parallelism between unextracted serum samples and purified samples. However, this method may allow the detection of as little as 20% of the total IGF-I in human serum and the proportion detected may vary depending upon the GH status of the patient. Also, the use of glass or polystyrene tubes, the presence of heparin, and the length of time the sample has stood at neutral or low pH all influence the ability of the antibody to detect antigen in the presence of IGFBPs.

An assay method for free IGF-I levels utilizing IGFBP-3 antibody to separate the IGF-I-BP complex from the free IGF-I in fluids and measuring free IGF-I by RIA is suggested by EP 375,438 published 27 Jun. 1990, page 8.

IGF samples can also be prepared for assay by acid-ethanol extraction. Baxter et al., *Clin. Chem.*, 28: 488-495 (1982); Daughaday et al., *J. Clin. Endocrinol. Metab.*, 781-788 (1980). The acid-ethanol extraction procedure has only been validated for human serum, and may not be fully effective on other sample types, or in different species. Thus, it may not remove all binding activity from human seminal plasma or from conditioned hepatocyte culture media. In the latter case the problem was overcome by adapting the acid gel chromatography technique to a high-pressure liquid chromatography with automated sample injection. Scott et al., *Endocrinology*, 116: 1094-1101 (1985).

As to measuring free IGF-I in the plasma, one of the traditional methods is to place the serum on a gel filtration column under neutral conditions, cut out fractions representing each peak obtained, and measure the free IGF-I level in each fraction by RIA. Unfortunately, this method is not sensitive due to extensive dilution, results in varying recovery levels, is subject to interference from some IGFBPs that overlap in peaks, and is time-consuming because only one sample at a time can be measured.

To overcome these problems, one method is to precipitate the IGFBPs and complexes and measure free IGF-I in the supernatant. Precipitation methods include ammonium sulfate or polyethylene glycol precipitation, or immunoprecipitation. However, precipitation may be incomplete or the free IGF-I may precipitate. Another method involves ultrafiltration of the serum [Daughaday et al., *J. Clin. Endocrin and Metab.*, 55: 916-921 (1982)] or equilibrium dialysis, which requires a long period of time and is not practical for large numbers of samples.

Another technique involves passing the serum through a small cartridge (e.g., Sep-Pak sold by Millipore) that retains the free IGF-I while allowing the bound IGF-I to flow through. Hizuka et al., 71st Endocrine Society Annual Meeting, Program Abstracts, 1989, Abst. #1020. The column is washed and eluted with organic solvent or acid to recover the free IGF-I. The resulting fraction is then concentrated (dried and lyophilized), reconstituted, and subjected to RIA. This technique suffers from variability in cartridges and recovery, the need for lyophilization or concentration, and impracticality. While this method allows analysis of more samples than the other methods, still only 30 to 40 samples a day can be processed.

Detection of other polypeptide hormones that circulate bound to one or more BPs has also been hampered by the above considerations. A well characterized such BP is the high-affinity growth hormone binding protein (GHBP) constituting the extracellular domain of the GH receptor that circulates in blood and functions as a GHBP in several species [Ymer and Herington, *Mol. Cell. Endocrino.*, 41: 153 (1985); Smith and Talamantes, *Endocrinology*, 123: 1489-1494 (1988); Emtner and Roos, *Acta Endocrinologica* (Copenh.), 122: 296-302 (1990)], including man. Baumann et al., *J. Clin. Endocrinol. Metab.*, 62: 134-141 (1986); EP 366,710 published 9 May 1990; Herington et al., *J. Clin. Invest.*, 77: 1817-1823 (1986); Leung et al., *Nature*, 330: 537-543 (1987). A second BP with lower affinity for GH has also been described that appears to be structurally unrelated to the GH receptor. Baumann and Shaw, *J. Clin. Endocrinol. Metab.*, 70: 680-686 (1990). Assays for, inter alia, GH are described e.g., in JP 86000941 published 13 Jan. 1986; JP 55037949 published 17 Mar. 1980; JP 85004423 published 4 Feb. 1985; DD 276,532 published 28 Feb. 1990; Ep 58,486 published 25 Aug. 1982; and U.S. Pat. Nos. 4,185,084 and 3,555,143.

Specific binding pairs (SBP), e.g., antigen-antibody, ligand-receptor, hormone-receptor, and lectin-oligosaccharide pairs, are discussed in U.S. Pat. No. 4,956,302. Assays of whole blood to detect a SBP member wherein a first member is immobilized prior to contact with the blood and the second member is detected through competition with labeled second member are reported in U.S. Pat. No. 4,594,327. A method to reduce interfering substances in assays of a SBP member wherein a SBP member is labeled and a receptor is used to capture both labeled and unlabeled SBP member is found in U.S. Pat. No. 4,737,456.

Further, free small analytes in samples are determined by absorbing at least a portion of the analyte with an insolubilized "receptor," washing the insoluble receptor, adding labeled sample analyte or receptor, incubating, washing the insoluble phase free of soluble phase, and determining the label, as described in U.S. Pat. No. 4,292,296. This method, along with the methods described by U.S. Pat. Nos. 4,680,275 and 4,704,355, utilizes antibodies or antigens as the receptor for the insoluble phase. Other solid-phase systems for ligand assays that involve determination of any analytes, not limited to those that circulate in complexed form, are described in U.S. Pat. Nos. 4,786,606 and 4,279,885. A method for detecting an inhibitor of a plasminogen activator wherein the activator may be immobilized is described in U.S. Pat. No. 4,791,068.

Other assay systems involving immobilized phases include those described by U.S. Pat. No. 4,015,939 (intermediate base anion exchange resin), U.S. Pat. No. 4,594,327 (assay for whole blood samples), U.S. Pat. No. 4,333,918 (assay for vitamin B12), U.S. Pat. No. 4,251,360 (utilizes tagged component), U.S. Pat. No. 4,219,335 (immunochemical testing assay), U.S. Pat. No. 4,005,187 (contacting two solutes in the fluid), U.S. Pat. No. 4,921,808 (assaying follicle stimulating hormone), U.S. Pat. No. 4,886,761 (polysilicon binding assay), U.S. Pat. No. 4,742,011 (assay device), and U.S. Pat. No. 4,943,522 (lateral flow assay), EP 166,623 (utilizes immunological reaction); JP 1098969 (immobilizing a soluble receptor); JP 62098260 (kit of enzyme-labeled antibody or antigen, protein, sheet to bind protein, substrate for the enzyme, and buffer liquid); and JP 85004423 (immobilizing receptor).

An object of the present invention is to provide an assay for free IGF-I, IGF-II, and GH in a body fluid that normally contains a proportion of IGF-I, IGF-II, and/or GH complexed with one or more binding proteins, which assay is not chromatographic and does not utilize an antibody as a capture reagent.

Another object is to provide an assay for such proteins that provides a number of advantages relating to ease and speed of analysis, reliability, sensitivity, selectivity, and precision.

These and other objects will be apparent to one of ordinary skill in the art.

SUMMARY OF THE INVENTION

Accordingly, this invention provides a method for determining levels of free ligand selected from the group consisting of IGF-I, IGF-II, and GH in a body fluid containing a proportion of the ligand bound to a binding protein comprising the steps of:

(a) contacting the body fluid with immobilized, unlabeled capture reagent under incubation conditions of 4°–10° C. for no greater than about 4 hours to bind the free ligand contained in the body fluid;

(b) separating the fluid from the immobilized capture reagent; and (c) measuring the level of free ligand bound to the capture reagent.

In another aspect, the invention provides a kit for determining the level of free ligand selected from the group consisting of IGF-I, IGF-II, and GH in a body fluid containing a proportion of the ligand bound to a binding protein comprising instructions, a capture reagent, a carrier solid phase for immobilization of the capture reagent, and a standard for the ligand, optionally also with a means for detecting the free ligand and a washing and incubation buffer.

Preferably, the ligand is IGF-I and the capture reagent is an IGF-I receptor or IGFBP-3, the detection step (c) of the assay method is performed using an ELISA, and the immobilization is on a microtiter plate.

DESCRIPTION OF THE PREFERRED EMBODIMENTS

Definitions

As used herein, "immobilized capture reagent" is a peptide, polypeptide, or protein that under normal circumstances in body fluids is in biological association or complexation with the ligand being assayed and binds to a site of that ligand, excluding antibodies to the ligand. The capture reagent may be purified from natural sources or produced by solid-phase protein synthesis or recombinant means. Immobilization means that the capture reagent is affixed to a carrier solid phase (solid support) as described further below. To maximize sensitivity of the assay, the capture reagent has an affinity for the ligand that is sufficiently high to bind any free ligand present in the body fluid to maximize sensitivity, but not so high as to strip and capture bound ligand from its endogenous BP-ligand complexes.

Also to maximize sensitivity, the capture reagent is a natural binding protein for the ligand, whether membrane bound or circulating, so that its affinity for the ligand will be the same as the affinity of the binding protein in the complex and its structure will be identical. Since the ligands have more than one binding protein, the capture reagent may be a mixture of the natural BPs in a ratio preferably reflecting the ratio occurring naturally in the body fluid. The preferred capture reagent is a specific binding protein with which a majority of the ligand is normally found complexed in the biological fluids of interest.

However, other polypeptides such as purified cellular receptors, polypeptide antagonists, and chromophores specific for the ligand are suitably employed if they have identical or similar affinities to the affinity of the major naturally occurring BP for the ligand and bind to the ligand in the general region where the major naturally occurring BP binds. The former can be determined by measuring and comparing the relative affinity and dissociation constants of the BP and candidate capture reagent. The latter can be determined by whether the purified BP competes with the receptor for the ligand, i.e., whether it inhibits the biological effects of the ligand in an in vitro test.

Examples of suitable receptors are the IGF-I and IGF-II receptors. It is known that purified BP-1 and BP-2 compete with the IGF receptors for IGF-I in several in vitro systems. Rutanen et al., *J. Clin. Endocrinol. Metab.*, 66: 1973–1980 (1988); Ross et al., *Biochem. J.*, 258: 267–272 (1989); Ritvos et al., *Endocrinology*, 12: 2150–2157 (1988); Pekonen et al., *J. Clin. Endocrinol., Metab.*, 67: 1250–1257 (1988). The IGF-I receptor would also be effective as capture reagent with IGFBP-3 as binding protein, which binds to IGF-I with similar affinity as the IGF-I receptor and can inhibit its activity. In contrast to the IGF-I receptors, IGF-II receptors do not bind insulin, and have very low affinity for IGF-I. Most cells studied appear to have IGF-I receptors or IGF-II receptors, or both of them. Another possible capture reagent for IGF-I is an inhibitory diffusible factor designated IDF45 that binds to IGF-I and inhibits its activity. EP 391,214 published 10 Oct. 1990.

The term "free ligand" refers to the analyte to be assayed, i.e., IGF-I, IGF-II, or growth hormone (preferably hGH), that is free from the BPs with which it is ordinarily associated or complexed in the body fluid being analyzed.

The term "binding protein" or "BP" refers to a protein or polypeptide normally associated with or bound or complexed to the ligand, whether or not it is circulatory, that does not elicit a biological response. Thus, such binding proteins do not include receptors that signal such response, but may include truncated non-membrane-bound cellular binding proteins that are sometimes called soluble receptors but have no biological function. Examples of such binding proteins include soluble GH receptor and IGF-II receptor. Others include specific binding proteins that are not related to receptors. These include, in the case of IGF, IGFBP-1, IGFBP-2, or IGFBP-3, and other identified IGF-I or IGF-II binding proteins [e.g., EP 375,438 published 27 Jun. 1990; EP 369,943 published 23 May 1990; WO 89/09268 published 5 Oct. 1989, Wood et al., *Molecular Endocrinology*, supra; Brinkman et al., *The EMBO J.*, 7: 2417–2423 (1988); Lee et al., supra; Brewer et al., *BBRC*, 152: 1289–1297 (1988); EP 294,021 published 7

Dec. 1988; Baxter et al., *BBRC*, 147: 408-415 (1987); Leung et al., *Nature*, 330: 537-543 (1987); Martin et al., *J. Biol. Chem.*, 261: 8754-8760 (1986); Baxter et al., *Comp. Biochem. Physiol.*, 91B: 229-235 (1988); WO 89/08667 published 21 Sep. 1989; WO 89/09792 published 19 Oct. 1989; and Binkert et al., *EMBO J.*, supra], and in the case of GH, the high-affinity GH binding protein [e.g., Ymer and Herington, *Mol. Cell. Endocrinol.*, supra] and low-affinity GH binding protein [Baumann and Shaw, *J. Clin. Endocrinol. Metab.*, supra].

The term "body fluid" refers to a biological sample of liquid containing the ligand. This sample may come from any mammal, but is preferably from a human. Such fluids include aqueous fluids such as serum, plasma, lymph fluid, synovial fluid, follicular fluid, seminal fluid, amniotic fluid, milk, whole blood, urine, cerebro-spinal fluid, saliva, sputum, tears, perspiration, mucus, tissue culture medium, tissue extracts, and cellular extracts.

MODES FOR CARRYING OUT THE INVENTION

Figure 1:
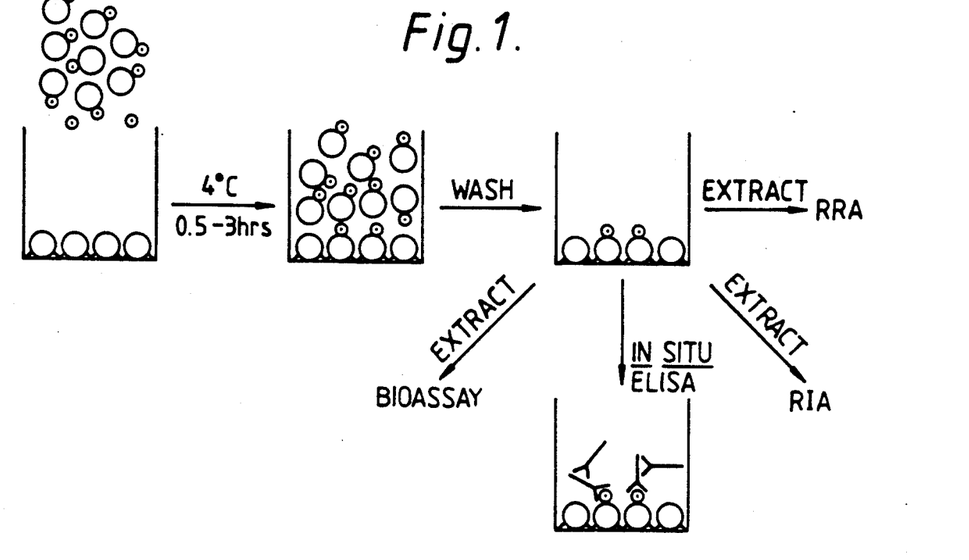
FIG. 1 depicts a cartoon illustrating the basic steps of the assay method of this invention, where the solid circle standing alone is free ligand, the open circle standing alone is the capture reagent, the open circle bound to the solid circle represents the complex of ligand bound to its BP in the body fluid, and the Y is antibody to the ligand.
Figure 2:
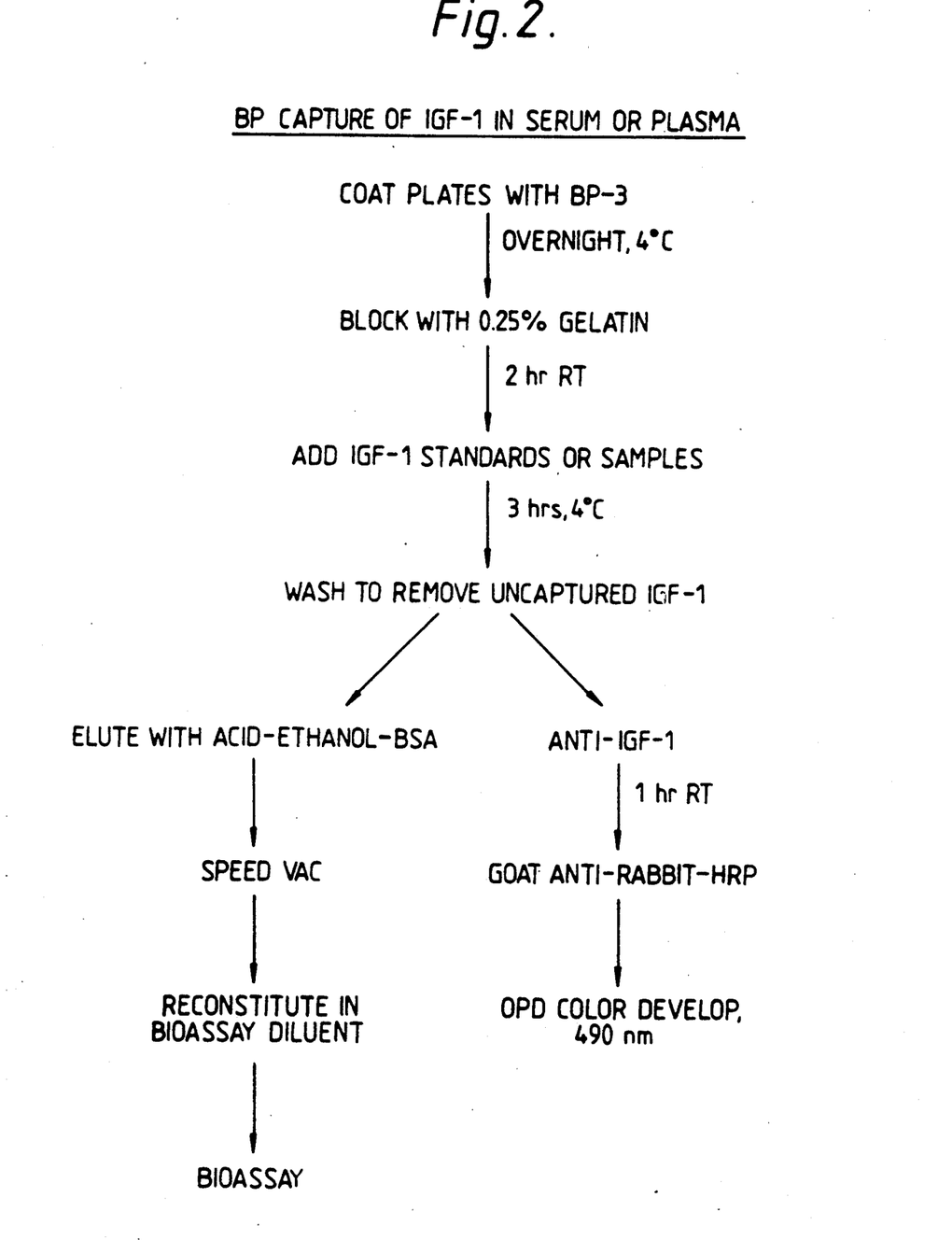
FIG. 2 illustrates a flow chart of IGFBP-3 capture of IGF-I in serum or plasma and detection by ELISA or bioassay, with suggested conditions, as one embodiment of the invention.

The method of this invention basically involves three steps, illustrated by the cartoon shown in FIG. 1 and by flow diagram in FIG. 2 for IGF-I/IGFBP-3 using bioassay or ELISA as the detection means.

First Step

In the first step, the body fluid is contacted and incubated with immobilized capture reagent. Immobilization conventionally is accomplished by insolubilizing the capture reagent either before the assay procedure, as by adsorption to a water-insoluble matrix or surface [U.S. Pat. No. 3,720,760] or non-covalent or covalent coupling [for example, using glutaraldehyde or carbodiimide crosslinking, with or without prior activation of the support with, e.g., nitric acid and a reducing agent (U.S. Pat. No. 3,645,852 or in Rotmans et al., *J. Immunol. Methods*, 57: 87-98 (1983))], or afterward, e.g., by immunoprecipitation.

The solid phase used for immobilization may be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. The preferred solid phase used is a multi-well microtiter plate that can be used to analyze several samples at one time. The most preferred is a microtest 96-well ELISA plate such as that sold as Nunc Maxisorb or Immulon.

The solid phase is coated with the capture reagent as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for 1 hour at room temperature.

Commonly used cross-linking agents for attaching the capture reagent to the solid phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates capable of forming cross-links in the presence of light.

If 96-well plates are utilized, they are preferably coated with the capture reagent (typically diluted in a buffer such as phosphate buffered saline (PBS)) by incubation for at least about 10 hours, more preferably at least overnight, at temperatures of about 4°-20° C., more preferably about 4°-8° C., and at a pH of about 6-8, more preferably about 6.5-7.5, and most preferably 7.2-7.4. If shorter coating times (1-2 hours) are desired, one can use 96-well plates with nitrocellulose filter bottoms (Millipore Multiscreen). The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, preferably about 1.5 to 3 hours.

After coating and blocking, the ligand standard (purified ligand) or the body fluid to be analyzed, appropriately diluted, is added to the immobilized phase. The amount of capture reagent employed is an optimal concentration sufficiently large to give a good signal in comparison with the ligand standards, but not in molar excess compared to the maximum expected endogenous BP level in the sample. For sufficient sensitivity, it is preferred that the amount of body fluid added be such that the immobilized capture reagent is in molar excess of the maximum molar concentration of free ligand anticipated in the body fluid after appropriate dilution of the body fluid. This anticipated level depends mainly on the particular ligand involved and any known correlation between the concentration levels of the free ligand in the particular body fluid being analyzed with the clinical condition of the patient. Thus, for example, hypoglycemic patients may have a maximum expected concentration of free IGF-I in their serum of 500 ng/ml, whereas a normal, non-hypoglycemic child or adult will be expected to have 10-20 ng/ml of free IGF-I in their serum based on what is known in the literature.

If too much of the capture reagent is present, however, the capture reagent will compete with the BP(s) present in the body fluid for the bound ligand, yielding inaccurate results. Thus, while the concentration of the capture reagent will generally be determined by the concentration range of interest of the ligand taking any necessary dilution of the body fluid into account, the final concentration of the capture reagent will normally be determined empirically to optimize the sensitivity of the assay over the range of interest. However, as a general guideline, the molar excess is suitably less than about ten-fold of the maximum expected molar concentration of free ligand in the body fluid after any appropriate dilution of the body fluid.

The conditions for incubation of sample and immobilized capture reagent are selected to optimize sensitivity of the assay. The temperature is generally from about 4° to 10° C. and the time depends on the temperature, being generally no greater than about 10 hours to avoid an insensitive assay. Preferably, the incubation time is from about 0.5 to 3 hours, and more preferably 1-3 hours at 4°-8° C. to maximize binding of free ligand to capture reagent. Usually constant temperatures are maintained during the incubation period.

At this stage, the pH of the incubation mixture will ordinarily be in the range of about 5-9, preferably in the range of about 6-8, and more preferably 7 to 7.5, depending mainly on the nature of the particular ligand and capture reagent employed. The pH of the incubation buffer is chosen to maintain a significant level of specific binding of the capture reagent to the ligand being captured. Various buffers may be employed to achieve and maintain the desired pH during this step, including borate, phosphate, carbonate, Tris-HCl or Tris-phosphate, citrate, acetate, barbital, and the like. The particular buffer employed is not critical to the invention, but in individual assays one buffer may be preferred over another.

Second Step

In the second step of the assay method herein, the body fluid is separated (preferably by washing) from the immobilized capture reagent to remove uncaptured ligand. The solution used for washing is generally a buffer ("washing buffer") with a pH that will depend on the ligand and capture reagent utilized, using the considerations and buffers described above for the incubation step, with a preferable pH range of 6-9. The washing may be done one or more times. The temperature of washing is generally from refrigerator to moderate temperatures, with a constant temperature maintained during the assay period, typically about 0°-40° C., more preferably about 4°-30° C. For example, the wash buffer can be placed in ice at 4° C. in a reservoir before the washing, and a plate washer can be utilized for this step. A cross-linking agent or other suitable agent may also be added at this stage to allow the now-bound ligand to be covalently attached to the capture reagent if there is any concern that the captured ligand may dissociate to some extent in the subsequent steps.

Third Step

In the last step of the assay method, the level of free ligand that is now bound to the capture reagent is measured using a detection means. This measurement may be accomplished by many techniques, such as extraction to remove the bound ligand from the capture reagent followed by bioassay, radioreceptor assay, or radioimmunoassay. Extraction may be carried out, for example, by acidic gel filtration or by chromatographic elution of the sample using acid-ethanol with or without bovine serum albumin as described in the literature. After elution, the solvent is evaporated as by using a speed vacuum, and the sample is reconstituted, e.g., by adding a suitable diluent for the assay in question.

Examples of bioassays that can be employed for IGF-I ligand include assays for cartilage-stimulating activity, insulin-like activity, and mitogenic activity such as DNA synthesis in porcine aortic smooth muscle cells or chick or mouse embryo and human fibroblasts. RRAs and RIAs for IGF-I and -II are as described in EP 128,733 published 19 Dec. 1984 and references cited in the background section above. Bioassays, RRAs, and RIAs for other ligands would be those conventional in the literature or known to those skilled in the art.

More preferably, however, the amount of free ligand is analyzed in the same plate, without the need for extraction or other cumbersome steps, using a standard ELISA method as detection means. This in situ ELISA method avoids the problems of recovery and variability of assay associated with the extraction method used in conjunction with the other assays. In this procedure, preferably a molar excess of an antibody with respect to the maximum concentration of free ligand expected (as described above) is added to the plate after it is washed. This antibody (which is directly or indirectly detectable) is preferably a polyclonal antibody, although any antibody can be employed. The affinity of the antibody must be sufficiently high that small amounts of the free ligand can be detected, but not so high that it causes the ligand to be pulled from the capture reagent.

The antibody and sample are incubated under conditions that minimize dissociation, including a pH that is suitable as described above. Preferably the incubation is accomplished at fairly constant temperatures ranging from about 0° C. to room temperature for about 0.5 to 3 hours, more preferably from about 4° C. to room temperature for about 0.5-2 hours, at a pH of preferably about 6 to 9.5. The duration of incubation may be longer if a protease inhibitor is added to prevent proteases in the biological fluid from degrading the ligand. If the antibody is very specific and sensitive, the incubation is typically carried out in 0.5 hour at room temperature.

Polyclonal antibodies to the ligand generally are raised in animals by multiple subcutaneous (sc) or intraperitoneal (ip) injections of the ligand and an adjuvant. It may be useful to conjugate the ligand to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The antibodies may be obtained from any convenient vertebrate source, such as murine, primate, lagomorpha, bovine, ovine, equine, canine, feline, or porcine. Chimeric antibodies may also be employed, as described, e.g., in U.S. Pat. No. 4,816,567; Morrison et al., *Proc. Natl. Acad. Sci. USA*, 81: 6851 (1984); Neuberger et al., *Nature*, 312: 604 (1984); Takeda et al., *Nature*, 314: 452 (1985). Chimeric antibodies are made by splicing the genes from a mouse antibody molecule of appropriate antigen specificity together with genes from another animal encoding a second antibody such as a human-derived gene.

Animals are immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant by subcutaneous injection at multiple sites. 7 to 14 days later animals are bled and the serum is assayed for anti-ligand titer. Animals are boosted until the titer plateaus. Preferably, the animal is boosted with the conjugate of the same ligand, but conjugated to a different protein and/or through a different cross-linking agent. Conjugates also can be made in recombinant cell culture as protein fusions. Also, aggregating agents such as alum are used to enhance the immune response. Methods for the production of polyclonal antibodies are described in numerous immunology textbooks, such as Davis et al., *Microbiology*, 3rd Edition, (Harper & Row, New York, New York, 1980).

Monoclonal antibodies are prepared by recovering spleen cells from immunized animals and immortalizing the cells in conventional fashion, e.g., by fusion with myeloma cells or by Epstein-Barr virus transformation, and screening for clones expressing the desired antibody. See, e.g., Kohler and Milstein, *Eur. J. Immunol.*, 6: 511 (1976). Monoclonal antibodies, or the antigen-binding region of a monoclonal antibody, such as Fab or (Fab)$_2$ fragments, may alternatively be produced by recombinant methods.

Examples of suitable antibodies include those already utilized in known RIAs for the protein in question, e.g., those antibodies directed against IGF-I described by Furlanetto et al., *J. Clin. Invest.*, supra; Bala and Bhaumick, supra; Zapf et al., *J. Clin. Invest.*, supra; Hintz et al., *J. Clin. Endocrinol. Metab.*, 51, 50, and 55, supra; and Hall et al., supra; and those antibodies directed against IGF-II described by, e.g., Zapf et al., *Metab. Clin. Exp.*, supra; Zapf et al., *Acta Endocrinol.*; Hintz and Liu, supra; Moses et al., supra.

Substitutes for antibodies may be employed in this technique provided that they bind specifically and do not bind to the ligand at the same site as the immobilized capture reagent.

The antibody added to the immobilized capture reagent will be either directly labeled, or detected indirectly by addition, after washing off of excess first antibody, of a molar excess of a second, labeled antibody directed against IgG of the animal species of the first antibody. The latter technique is preferred since the labeling procedure involving chemical reactions may perturb the specificity and/or affinity of the first antibody. In the latter, indirect assay, labeled antisera against the first antibody are added to the sample so as to produce the labeled antibody in situ.

The label used for either the first or second antibody is any detectable functionality that does not interfere with the binding of free ligand to the antibody. Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, $\beta$-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bisimidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, New York, 1981), pp. 147–166.

Following the addition of last labeled antibody, the amount of bound antibody is determined by removing excess unbound labeled antibody through washing and then measuring the amount of the attached label using a detection method appropriate to the label, and correlating the measured amount with the amount of free ligand in the body fluid. For example, in the case of enzymes, the amount of color developed and measured will be a direct measurement of the amount of ligand present. Specifically, if HRP is the label, the color is detected using the substrate OPD at 490 nm absorbance.

In one example, after an enzyme-labeled second antibody directed against the first unlabeled antibody is washed from the immobilized phase, color or chemiluminiscence is developed and measured by incubating the immobilized capture reagent with a substrate of the enzyme. Then the amount of free ligand concentration is calculated by comparing with the color or chemiluminescence generated by the standard ligand run in parallel.

As a matter of convenience, the assay method of this invention can be provided in the form of a kit, i.e., a packaged combination of instructions for carrying out the assay, capture reagent as defined above, standards for the ligand (i.e., purified ligand, preferably recombinantly produced ligand), and solid support for immobilization as defined above. In addition, a detection means as defined above may be included, such as a specific antibody to the ligand, which is labeled or unlabeled, as well as other additives such as stabilizers, washing and incubation buffers, and the like.

Examples of standards for IGF-I are recombinant human IGF-I produced in *E. coli*, as described by EP 230,869 published 5 Aug. 1987, or available commercially from KabiGen AB, Stockholm, Sweden (specific activity > 14,000 U/mg by radioreceptor assay using placental membranes), or available for clinical investigations from Genentech, Inc., South San Francisco. Examples of standards for GH are recombinant methionyl human growth hormone (Protropin ® brand, Genentech, Inc., South San Francisco, Calif.) and recombinant human growth hormone lacking the N-terminal methionine (Nutropin ® brand, Genentech, Inc.).

The preferred detection means is detectable antibodies directed against the ligand. Such antibodies are preferably unlabeled antibodies and antibodies directed against the unlabeled antibodies raised in a different species and containing a detectable label. Where the label is an enzyme, the kit will ordinarily include substrates and cofactors required by the enzyme, and where the label is a fluorophore, a dye precursor that provides the detectable chromophore.

The component of the kit will be provided in predetermined ratios, with the relative amounts of the various reagents suitably varied to provide for concentrations in solution of the reagents that substantially optimize the sensitivity of the assay. Particularly, the reagents may be provided as dry powders, usually lyophilized, including excipients, which on dissolution will provide for a reagent solution having the appropriate concentration for combining with the sample to be tested.

The following examples are intended to illustrate one embodiment now known for practicing the invention, but the invention is not to be considered limited to these examples. All open and patented literature citations herein are expressly incorporated by reference.

EXAMPLE I

A total of 1-6 μg/ml of recombinant IGFBP-3 (expressed in mammalian cells and purified as described in WO 89/09268 published 5 Oct. 1989 and Wood et al., *Molecular Endocrinology*, supra) was diluted in phosphate-buffered saline (PBS) and 50 μl were added per well in 96-well microtiter plates (Immulon). After overnight incubation at 4°-8° C., unsaturated binding sites on the plastic surface were blocked with 0.25% gelatin. Eighteen samples of IGF-I standard (recombinant human IGF-I produced in *E. coli* by the process generally described in EP 230,869 published Aug. 5, 1987, or available commercially from KabiGen AB, Stockholm, Sweden (specific activity > 14,000 U/mg by radioreceptor assay using placental membranes), or available for clinical investigations from Genentech, Inc., South San Francisco) and plasma samples from three human patients were diluted in "capture buffer" consisting of PBS, 0.1% gelatin, 5 mM EDTA, and 0.2-0.4 TIU (Trypsin Inhibitory Units)/ml aprotinin, pH 7.2. Fifty μl of each of these diluted standards or samples was added to each well and incubated for 45 min. to 3 hours at 4°-8° C. with shaking. The wells were then quickly washed with 3×0.2 ml "wash buffer" of PBS, 0.05% Tween-20, and 0.01% merthiolate, pH 7.2. Then, 0.1 ml of appropriately diluted (ca. 1:1000) IGF-I antibody (prepared by immunizing rabbits with IGF-I linked to Keyhole Limpet Hemocyanin) in PBS+0.1% gelatin buffer was added. After one hour shaking at room temperature, excess IGF-I antibody was removed with 3×0.2 ml wash buffer. 100 μl of appropriately diluted (ca. 1:2000) goat anti-rabbit-HRP conjugate (Cappel Laboratories) was added to the wells and incubated further for 0.5-1 hour. Excess unbound goat anti-rabbit-HRP conjugate was removed with 3×0.2 ml wash buffer. Color was developed by adding 0.1 ml of HRP substrate (OPD, Sigma) and incubating for 15-60 min. Color reaction was stopped with 0.1 ml of 4.5N sulfuric acid and the color was read on a plate reader at 490 nm.

Figure 3:
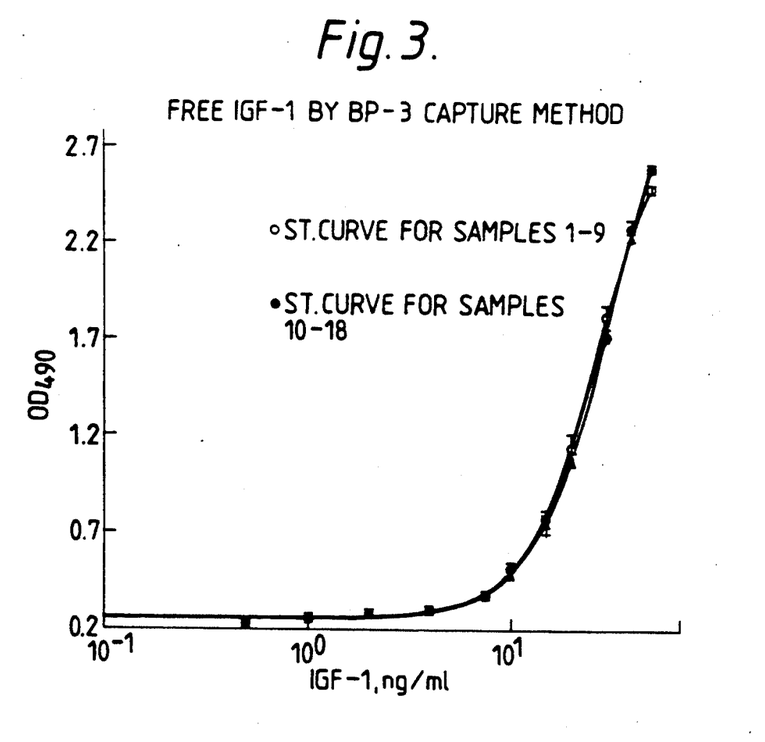
FIG. 3 illustrates a graph of the concentration of free IGF-I versus absorbance of the enzyme product at 490 nm as measured using IGFBP-3 as the capture reagent.

The standard curves on two different plates are shown in FIG. 3. Recoveries of IGF-I exogenously added to plasma ranged from 70-90%. Normal human plasma (EDTA) had free IGF-I in the range of 5-25 ng/ml. Three assays were used to measure either total or free IGF-I in plasma of human volunteers injected with a bolus iv injection of recombinant human IGF-I. Total IGF-I in each of the patient samples was determined by RIA using standard RIA methods, e.g., Furlanetto and Marino, *Methods in Enzymol.*, 146: 216-226 (1987). Free IGF-I was determined by the standard HPLC-RIA method described in Celnicker et al., 72nd Annual Meeting of Endocrine Soc., Prog. Abstract No. 1144 (1990) or by the assay method as described above.

The results of the RIA for total IGF-I, and the HPLC-RIA and IGFBP-3 capture techniques for free IGF-I are shown in Table 1. It can be seen that free IGF-I levels in these cases reached 222-428 ng/ml within 2-6 minutes after injection and fell to <5-36 ng/ml after 3.5-4 hours. Total IGF-I measured under these conditions was 368-555 ng/ml in 2-6 minutes and 156-251 ng/ml after 3.5-4 hours. This pattern of IGF-I levels was identical to that obtained using the gel filtration-RIA method.

It can be seen from Table 1 that the method herein for determining free IGF-I levels in plasma using IGFBP-3 is far more sensitive than the method using HPLC-RIA, and the values for free IGF-I are closer to the expected values. The sensitivity of the method using the polyclonal rabbit anti-IGF-I and goat anti-rabbit IgG-HRP conjugate as detection system is about 5 ng/ml. Even higher sensitivities are obtainable using higher affinity IGF-I antibodies and other detection systems such as alkaline phosphatase-chemiluminescence.

TABLE 1

IGF-I measured by HPLC-RIA method vs IGF BP-3 capture method

| Patient # | Minutes after IGF-I injection | Total (RIA) | Free | | |
|---|---|---|---|---|---|
| | | | HPLC-RIA | BP-3 capture | Theoretical |
| 535-001 | 2 | 555 | 290 | 428 ± 21 | 555-93* = 462 |
| | 210 | 167 | L | <20 | |
| | 240 | 156 | L | 22 ± 16 | |
| | 2 | 517 | 236 | 347 ± 14 | 517-140* = 377 |
| | 210 | 235 | L | 36 ± 9 | |
| | 240 | 223 | L | 30 ± 6 | |
| 535-002 | 6 | 380 | 135 | 222 ± 9 | 380-163* = 217 |
| | 210 | 163 | L | 9 ± 7 | |
| | 240 | 164 | L | 34 ± 2 | |
| | 4 | 372 | 126 | 313 ± 13 | 327-163* = 211 |
| | 210 | 230 | L | <5 | |
| | 240 | 251 | L | <5 | |
| 535-003 | 4 | 368 | 179 | 255 ± 14 | 368-104* = 264 |
| | 210 | 199 | L | <5 | |
| | 240 | 175 | L | <5 | |
| | 2 | 571 | 303 | 459 ± 39 | 571-188* = 383 |
| | 210 | 251 | L | 13 ± 13 | |

TABLE 1-continued

| | | | IGF-I measured by HPLC-RIA method vs IGF BP-3 capture method | | |
|---|---|---|---|---|---|
| Patient # | Minutes after IGF-I injection | Total (RIA) | Free | | Theoretical |
| | | | HPLC-RIA | BP-3 capture | |
| | 240 | 212 | L | 34 ± 4 | |

*Preinjection total IGF-I

The method shown by this invention has a high throughput (300–400 samples for free IGF-I in 8 hours) and is less prone to errors, because all the steps are carried out in the same well.

Figures 4, 4A:
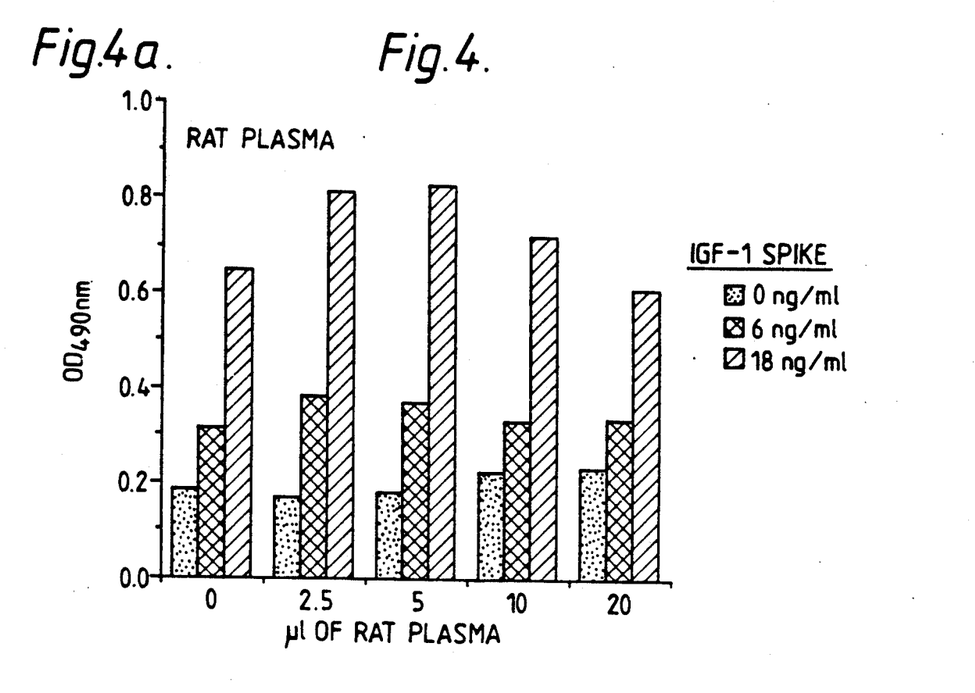
FIG. 4a illustrates a bar graph of μl of rat plasma versus absorbance at 490 nm for 0, 6, and 18 ng/ml IGF-1 spike.
Figure 4B:
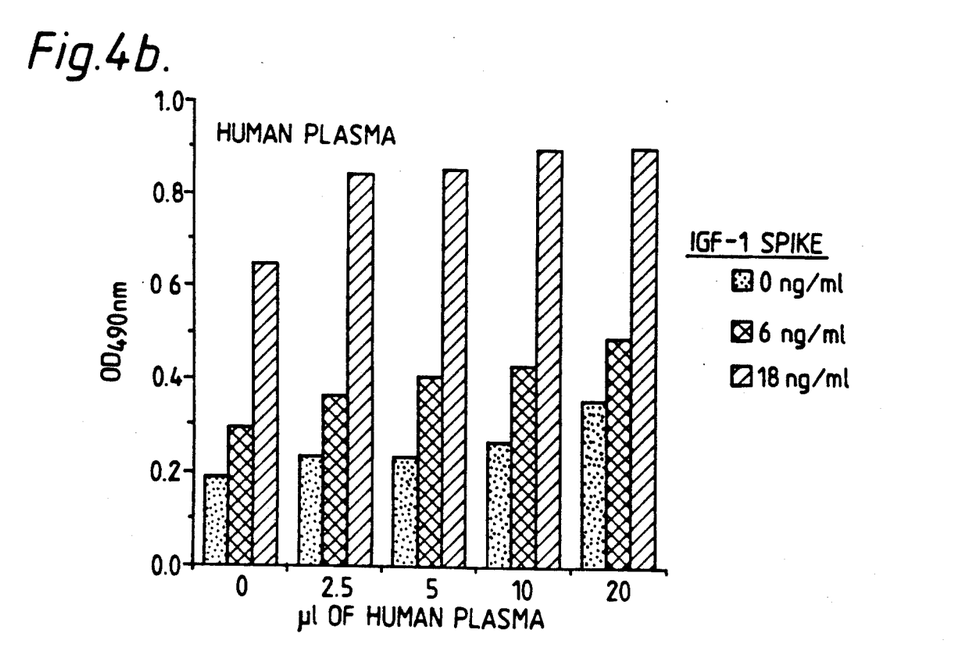
FIG. 4b is the same as FIG. 4a except that the plasma is human plasma.

FIG. 4 shows the amount of free IGF-I levels (from OD at 490 nm) obtained when the procedure described above was employed using as test samples various amounts of a rat (FIG. 4a) or human (FIG. 4b) plasma sample untreated or spiked with 60 or 180 ng/ml of IGF-I and diluted 1:10 before adding to the assay wells. It is seen that the recovery of spiked IGF-I by this assay method is good and reliable.

Similar results would be expected if the experiment was repeated wherein the capture reagent is covalently attached to the microtiter plate; and/or the captured IGF-I is covalently linked to the capture reagent; or IGF-II antibody is used in place of IGF-I antibody to measure free IGF-II; or the major GH binding protein (GHBP-1) is used to capture free GH in serum or plasma.

EXAMPLE II

The procedure of Example I was repeated except that a partially purified IGF-I receptor was used as capture reagent instead of IGFBP-3 and the test sample was a human patient sample untreated or spiked with 50, 100, or 200 ng/ml of IGF-I and diluted 1:10 before adding to the assay wells. Preparation of the cellular membrane containing the receptor, solubilizing using Triton-X100, passing through a wheat-germ agglutinin Sepharose column, and eluting with N-acetylglucose amine were carried out essentially using the method for preparing insulin receptor as described by Yamaguchi et al., *J. Biol. Chem.*, 258: 5045–5049 (1983).

The amount of free IGF-I in the unspiked and spiked plasma samples was determined, along with percent recovery. The results are shown in Table 2. It can be seen that good recovery of the added IGF-I was obtained, particularly when 10 ng/ml was added, and that the method is also sensitive and reliable using the receptor rather than the binding protein as capture reagent. Even better sensitivity and recovery levels can be expected if the receptor is further purified by methods such as those described by LeBon et al., *J. Biol. Chem.*, 261: 7685–7689 (1986).

TABLE 2

| IGF-I capture from plasma by Immobilized IGF-I Receptor | | |
|---|---|---|
| Sample | IGF-I measured ng/ml | % Recovery |
| Plasma (P) | 2.7 ± 0.66 | — |
| P + IGF-I, 5 ng/ml | 6.8 ± 0.95 | 82 |
| P + IGF-I, 10 ng/ml | 11.5 ± 0.72 | 88 |
| P + IGF-1, 20 ng/ml | 18.0 ± 1.30 | 76 |

What is claimed is:

1. A method for determining levels of free ligand selected from the group consisting of insulin-like growth factor-I (IGF-I), insulin-like growth factor II (IGF-II), and growth hormone (GH) in a body fluid containing a proportion of the ligand bound to a binding protein comprising the steps of:

(a) contacting the body fluid with immobilized, unlabeled capture reagent, which capture reagent is insulin-like growth factor binding protein-3 (IGFBP-3) if the ligand is IGF-I or IGF-II, or growth hormone binding protein (GHBP) if the ligand is GH, under incubation conditions of 4°–10° C. for no greater than about 4 hours to bind the free ligand contained in the body fluid;

(b) separating the fluid from the immobilized capture reagent; and (c) measuring the level of free ligand bound to the capture reagent.

2. The method of claim 1 wherein the body fluid is serum or plasma.

3. The method of claim 1 wherein in step (a) the body fluid is contacted with a molar excess, with respect to the maximum expected molar concentration of free ligand in the body fluid after dilution, of the immobilized unlabeled capture reagent.

4. The method of claim 3 wherein the molar excess is less than ten-fold of the maximum expected molar concentration of free ligand in the body fluid after dilution.

5. The method of claim 1 wherein the capture reagent is coated on a 96-well microtiter plate.

6. The method of claim 5 wherein after the coating step the microtiter plate is contacted with a non-specific blocking agent for a period of time sufficient to block the excess binding sites of the plate.

7. The method of claim 6 wherein the blocking agent is gelatin, bovine serum albumin, egg albumin, or casein.

8. The method of claim 1 wherein step (a) is carried out for about 0.5 to 3 hours.

9. The method of claim 1 wherein step (b) is carried out at about 4°–30° C.

10. The method of claim 1 wherein the measuring step is carried out by the steps comprising:

(d) incubating the immobilized capture reagent with detectable antibodies to the ligand;

(e) separating the detectable antibodies from the immobilized capture reagent to remove excess unbound antibodies;

(f) measuring the amount of bound detectable antibodies; and (g) correlating the measured amount in step (f) with the amount of free ligand bound to the capture reagent.

11. The method of claim 10 wherein the detectable antibodies contain a label selected from the group consisting of an enzyme, radioactive label, fluorescent label, spin label, bacteriophage label, and chemiluminescent label.

12. The method of claim 11 wherein the label is an enzyme selected from the group consisting of horseradish peroxidase, glucoamylase, glucose-6-phosphate dehydrogenase, glucose oxidase, lysozyme, beta-galactosidase, or alkaline phosphatase.

13. The method of claim 10 wherein the antibodies bound to the ligand are detected by contact with labeled antisera directed against the antibodies.

14. The method of claim 1 wherein the measuring step is carried out by extracting the free ligand from the capture reagent and assaying for levels of free ligand.

15. The method of claim 14 wherein the assay is a radioreceptor assay, bioassay, or radioimmunoassay.

16. A method for determining levels of free insulin-like growth factor-I (IGF-I) in a body fluid containing a proportion of the IGF-I bound to a binding protein comprising the steps of:
  (a) contacting the body fluid with immobilized, unlabeled insulin-like growth factor binding protein-3 (IGFBP-3) under incubation conditions of 4°–10° C. for no greater than about 4 hours to bind the IGF-I contained in the body fluid;
  (b) separating the fluid from the immobilized IGFBP-3; and
  (c) measuring the level of IGF-I bound to the IGFBP-3.

17. A kit for determining the level of free ligand selected from the group consisting of insulin-like growth factor-I (IGF-I) and insulin-like growth factor-II (IGF-II) in a body fluid containing a proportion of the ligand bound to a binding protein comprising instructions, a capture reagent that is insulin-like growth factor binding protein-3 (IGFBP-3), a carrier solid phase for immobilization of the capture reagent, and a standard for the ligand.

18. The kit of claim 17 further comprising a means for detecting the free ligand.

19. A kit for determining the level of free IGF-I in a body fluid containing a proportion of the IGF-I bound to a binding protein comprising instructions, insulin-like growth factor binding protein-3 (IGFBP-3), a carrier solid phase for immobilization of the IGFBP-3, and a standard for the IGF-I.

* * * * *